United States Patent [19]
Dorsel et al.

[11] Patent Number: 5,673,096
[45] Date of Patent: Sep. 30, 1997

[54] INTERFEROMETRIC ARRANGEMENT WITH DIFFRACTIVE OPTICAL ELEMENT FOR MEASURING INTRAOCULAR DISTANCES

[75] Inventors: Andreas Dorsel, Menlo Park, Calif.; Karl-Heinz Donnerhacke; Beate Moeller, both of Jena, Germany

[73] Assignee: Carl Zeiss Jena GmbH, Jena, Germany

[21] Appl. No.: 578,095

[22] Filed: Dec. 26, 1995

[30] Foreign Application Priority Data

Dec. 23, 1994 [DE] Germany .......................... 44 46 183.6

[51] Int. Cl.$^6$ ................................................. A61B 3/10
[52] U.S. Cl. ........................... 351/211; 351/205; 351/221
[58] Field of Search ................................... 351/205, 211, 351/221, 246, 200

[56] References Cited

U.S. PATENT DOCUMENTS 5,349,399  9/1994  Sekine ..................................... 351/221

FOREIGN PATENT DOCUMENTS 0509903   10/1992   European Pat. Off. .
WO92/19930 11/1992  WIPO .

OTHER PUBLICATIONS

"ABC der Optik", Leipzig 1961, pp. 96–99.
"Laser Beam Lithographed Micro–Fresnel Lenses," *Applied Optics*, vol. 29, No. 34, 1 Dec. 1990, pp. 5120 to 5126.
"Fabrication of Holographic Microlenses Using a Deep UV Lithographed Zone Plate," *Applied Optics*, vol. 29, No. 34, 1 Dec. 1990, pp. 5111 to 5114.
"Wavelength Independent Grating System," *Applied Optics*, vol. 28, No. 4, 15 Feb. 1989, pp. 682 to 686.

*Primary Examiner*—Hung X. Dang
*Attorney, Agent, or Firm*—McAulay Fisher Nissen Goldberg & Kiel, LLP

[57] ABSTRACT

An arrangement for measuring intraocular distances between different optical boundary surfaces of the human eye by at least one interferometric measurement system is provided. The arrangement further comprises at least one diffractive optical element (DOE) for dividing the illumination beam path into partial beam paths for different boundary surfaces and/or for combination and mutual adaptation of the wavefronts of measurement light components proceeding from different boundary surfaces and/or for adaptation of the wavefronts of measurement light components proceeding from different boundary surfaces of the eye to the wavefront of the measurement light of at least one interferometric reference arm.

21 Claims, 4 Drawing Sheets

PHASE FRESNEL LENS

INTERFEROMETRIC ARRANGEMENT WITH DIFFRACTIVE OPTICAL ELEMENT FOR MEASURING INTRAOCULAR DISTANCES

BACKGROUND OF THE INVENTION a. Field of the Invention

The invention is directed to an arrangement for measuring intraocular distances between different optical boundaries by at least one intraocular system.

b. Description of the Related Art

It is already known (from DE 3201801) to unite the light of a light source of short coherent length, which light is reflected from a first boundary surface or interface of the eye, with the light reflected from another boundary surface in an observation beam path by means of an interferometric arrangement, wherein the difference in the optical wavelengths of the reflected light components is compensated for via a displaceable mirror. In so doing, the displacement of the mirror serves as a measurement for the distance between the analyzed boundary surfaces.

Further, it is known, e.g., from "Lasers in Surgery and Medicine" 13:447–452 (1993), to direct an illumination beam path, e.g., by means of a laser diode, onto the eye via an interferometric arrangement with an adjustable difference in wavelength between interferometric partial beams and to detect the occurring interference of the radiant components reflected by different boundary surfaces of the eye by means of a photodetector arrangement depending on the adjustment of the difference in wavelength.

A divergent spherical wave caused by reflection at the cornea of the eye and an approximately plane wave which originates from the light reflected at the retina are overlapped and produce a pattern of circular interference fringes. The diameter of the individual circular fringes varies with the distance of the observing plane from the center of curvature of the surface of the cornea. Only the light from the central interference fringe, i.e., usually only a fraction of the light containing information on measurement values, reaches the detector.

In WO 92/19930, by means of a displaceable reflector, the specimen or the eye itself forms a first arm of an interferometer arrangement with a difference in optical wavelength which can be adjusted in a second arm by means of a displaceable reflector, wherein the radiant components of the interferometer arms are brought to interference and the interference signal is detected.

EP 509903, U.S. Pat. No. 5,347,328, and U.S. Pat. No. 5,347,327 provide separate illumination beam paths and/or measurement beam paths and independent interferometer arrangements for different interface layers or boundary layers of the eye, wherein separate reference surfaces can be provided for the individual boundary layers of the eye and an additional reference interferometer arrangement can be provided.

By changing the wavelength in the interferometer containing the measured object and in a reference interferometer with a fixed optical wavelength difference, and by evaluating the mixed interference signals, it is possible to determine axial length.

Similar arrangements for length measurement incorporating a plurality of wavelengths are described in U.S. Pat. No. 4,907,886.

In IEEE Photonics Technology Letters, Vol. 5, No. 6, Jun. 1993, an attempt was made to improve the signal-to-noise ratio by combining a partially reflecting plane plate with a lens having an aperture.

OBJECT AND SUMMARY OF THE INVENTION

The primary object of the present invention is to realize ocular length measurement with an improved measurement signal and to simplify existing systems.

This object is met according to the invention by at least one diffractive optimal element (DOE) for dividing illumination beam path into partial beam paths for different boundary surfaces and/or for combination and mutual adaptation of the waveforms of measurement light components proceeding from different boundary surfaces and/or for adaptation of the wavefronts of measurement light components proceeding from different boundary surfaces of the eye to the wavefront of the measurement light of at least one interferometric measurement arm.

Other features of the invention are directed in a particularly advantageous manner to interferometric arrangements for axial ocular length measurement with an adjustable difference in optical wavelength and also, surprisingly, to the simplification of measurement arrangements with a variable wavelength and evaluation of mixed interference signals with respect to the dividing of the illumination light components with a diffractive optical element and with respect to the mutual adaptation of the wavefront shapes of waves reflected by different boundary surfaces of the human eye or adaptation to the wavefront of the light of waves reflected by a reference surface.

The diffractive optical element which is similar in shape to a phase fresnel lens generates the retina signal by means of a component of the measurement light which is not acted upon, i.e., a collimated component striking the eye, and the cornea signal, for example, is generated by the diffractive optical element by means of a component which is acted upon, i.e., a convergent component striking the eye, in that this component is focussed via the DOE (diffractive optical element) on the corneal vertex, on the focal point of the convex corneal image or on the center of curvature of the convex corneal image.

This results in substantially more favorable preconditions for obtaining signals, since the retina signal and the cornea signal are adapted, e.g., in collimated form, with respect to their wavefronts by passing repeatedly through the DOE and accordingly the component of the bundle cross section which can be used to obtain signals is substantially greater than it would be if the wavefronts were not adapted.

Further advantages and results of the invention and the construction of a measurement arrangement according to the invention are described more fully in the following with reference to the schematic drawings.

DESCRIPTION OF THE PREFERRED EMBODIMENTS

Figure 1:
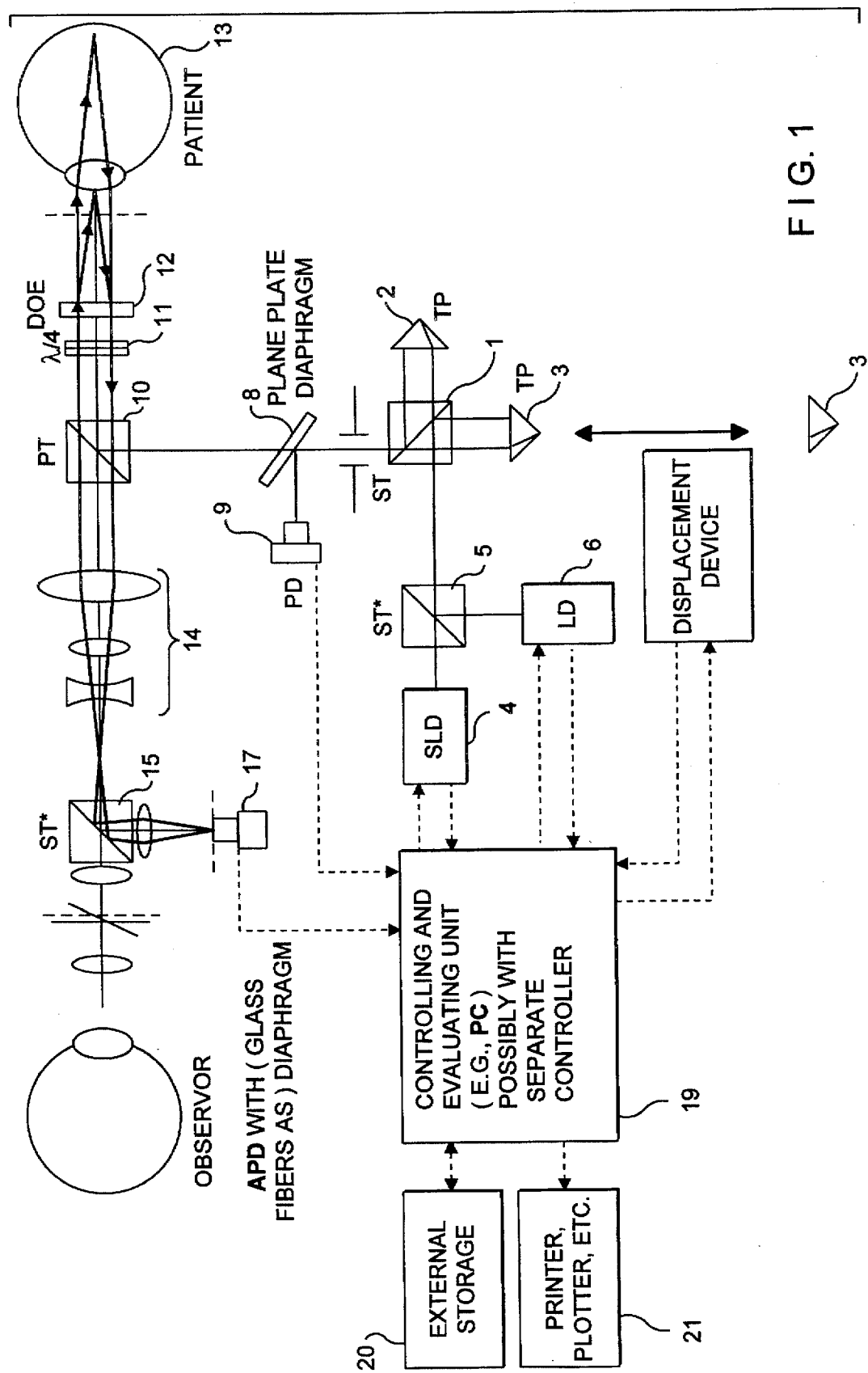
FIG. 1 is an overall view of a measurement arrangement according to the invention with adjustable difference in optical wavelengths.

In FIG. 1, a beam divider 1 with a triple prism 2 and a displaceable triple prism 3 forms an interferometer arrangement in which the light of a superluminescence diode 4 or a laser diode 6, optionally, is radiated via another beam divider 5 as a measurement light source or adjustment light source.

Figure 2:
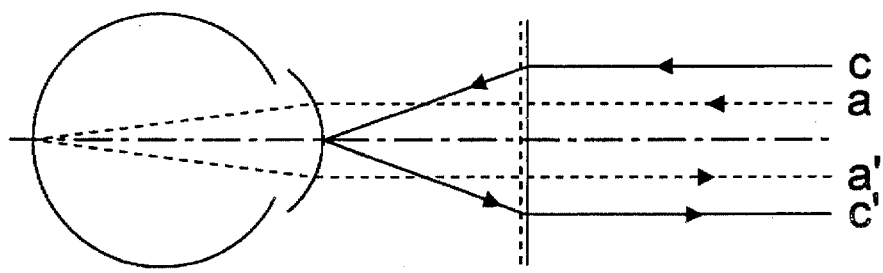
FIG. 2 is a schematic view of the beam path when focussing on the corneal vertex.
Figure 4:
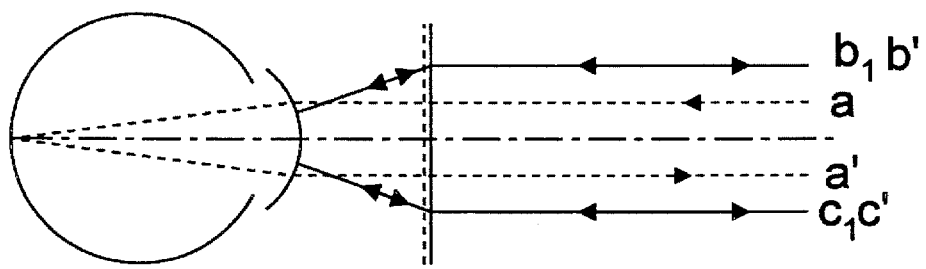
FIG. 4 is a schematic view of the beam path when focussing on the center of curvature of the corneal image.
Figure 3:
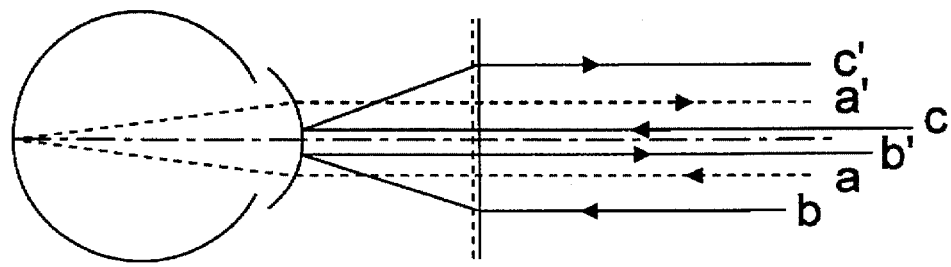
FIG. 3 is a schematic view of the beam path when imaging the focal point of the convex corneal image.

By way of a diaphragm 7 and a plane plate 8 for cutting out a control component on a photo diode 9, the illumination light strikes the eye 13 via a polar beam divider 10, a$\lambda$/4-plate 11, and a DOE 12. A portion of the illumination light is focussed on the corneal vertex, the focal point of the convex corneal image or the center of curvature of the convex corneal image by means of the DOE 12 as is shown in FIGS. 2, 3 and 4, while the other parallel beam component which is not acted upon is imaged on the retina of the eye. The exact course of the radiated and reflected beam components is described more fully with reference to FIGS. 2, 3 and 4.

The light which is reflected by the eye and collimated is imaged via the polar beam divider 10, a $\lambda$/4-plate, and an imaging system 14 via a beam divider 15 in an observation plane in which, e.g., the sensor surface of a CCD camera can be arranged or on a photodetector 17, preferably an avalanche photodiode. The divergent components which are not used can be cut out.

The light sources 4 and 6, a displacement device 18 for displacing the triple prism 3, and the photodetectors 9, 17 are coupled with a controlling and evaluating unit 19 which can be connected with external storages 20 and a printer 21.

FIGS. 2 to 4 show a more detailed view of the beam path of incident and reflected radiation according to FIG. 1.

The approximately plane wave, which strikes the DOE 12 via the polar beam divider 10 and $\lambda$/4-plate 11, is partially focussed by this DOE 12 and remains partially collimated without being changed.

In FIG. 2, the partial bundle a, a' of the collimated illumination beam which is not influenced by the DOE is imaged on the retina by the optical effect of the front ocular media and exits the eye as a collimated bundle which remains substantially unaffected after passing repeatedly through the DOE. The partial bundle c, c' of the illumination beam influenced by the DOE is focussed on the corneal vertex. The divergent bundle reflected at the cornea is at least partially collimated again after passing repeatedly through the DOE. The focus for the measurement light advantageously lies in the focal plane of the observation optical system. As a result of this, the convergent spherical wave is reflected back into itself exactly at the cornea when the observation optical system is adjusted on the corneal vertex.

Alternatively, according to FIG. 3, it would be possible to focus the observation optical system on the focal point of the convex corneal image. The convergent partial bundle b, b' of the illumination beam which is influenced by the DOE is reflected by the cornea surface as a collimated bundle and passes through the DOE so as to be at least partially unaffected as bundle c, c'. The partial bundle a, a' which is not affected by the DOE partially penetrates the eye and is imaged on the retina by the optical action of the front ocular media and exits the eye again as a collimated bundle which remains substantially unaffected by the DOE. The component of the partial bundle a, a' reflected at the surface of the cornea reaches the DOE as a divergent bundle and is at least partially collimated again by the latter.

FIG. 4 shows the focussing on the center of curvature of the corneal image. The convergent partial beam bundle b, b' which is acted upon by the DOE is reflected on itself at the cornea surface and is at least partially collimated again after passing repeatedly through the DOE. The collimated partial bundle a, a' which is not affected by the DOE is focussed on the retina as was already described above and exits the eye as a collimated bundle which remains at least partially unaffected by the DOE.

In addition, the construction according to FIGS. 2–4 effects a substantially uncritical lateral positioning of the apparatus relative to the eye. A particularly advantageous use of a short-coherent light source for the measurement light enables a simple adjustment of the construction to maximum, approximately infinite fringe width. The returning collimated interfering beam components are imaged on a detector by an imaging optical system; the other beam components which are not collimated can be cut out.

Figure 5:
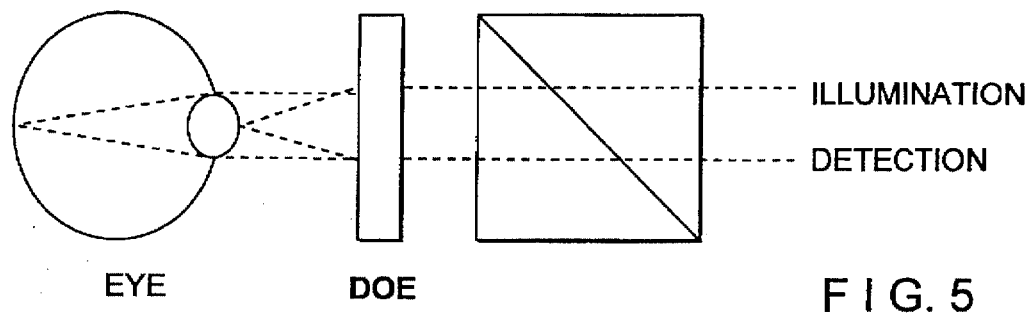
FIG. 5 is a schematic view of the arrangement of a DOE upstream of a combined illumination beam path and measurement beam path of an interferometric measurement arrangement.

In FIG. 5, independent interferometer arrangements can also be provided in the illumination beam path and measurement beam path with external reference surfaces with mixing of the interference signals and alteration of the wavelengths according to U.S. Pat. No. 5,347,327 and EP 509903, wherein separate optical channels for separate adaptation of illumination light and/or measurement light can be avoided by using the DOE, which leads to a considerable simplification.

According to WO 92/19930, the eye can also be arranged in an arm of the interferometer arrangement which further contains a displaceable reference surface, wherein a short-coherent light source is provided.

Further, FIG. 5 can contain an illumination beam path and measurement beam path according to the view shown in FIG. 1.

Figure 6:
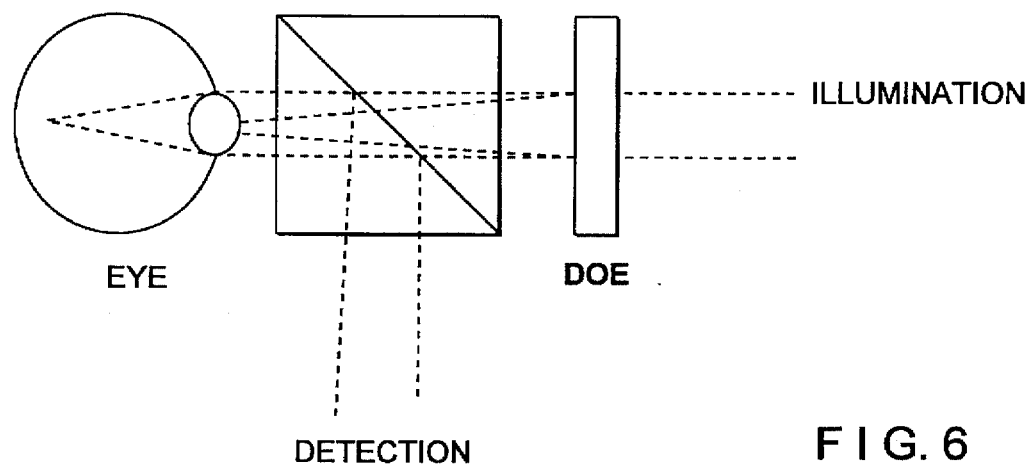
FIG. 6 is a schematic view of the arrangement of a DOE in the illumination beam path for dividing the illumination.

In FIG. 6, the DOE is arranged in the illumination beam path and serves only for advantageously dividing the illumination light on different boundary layers of the eye, while the measurement light reaches a detection beam path via a beam divider.

Figure 7:
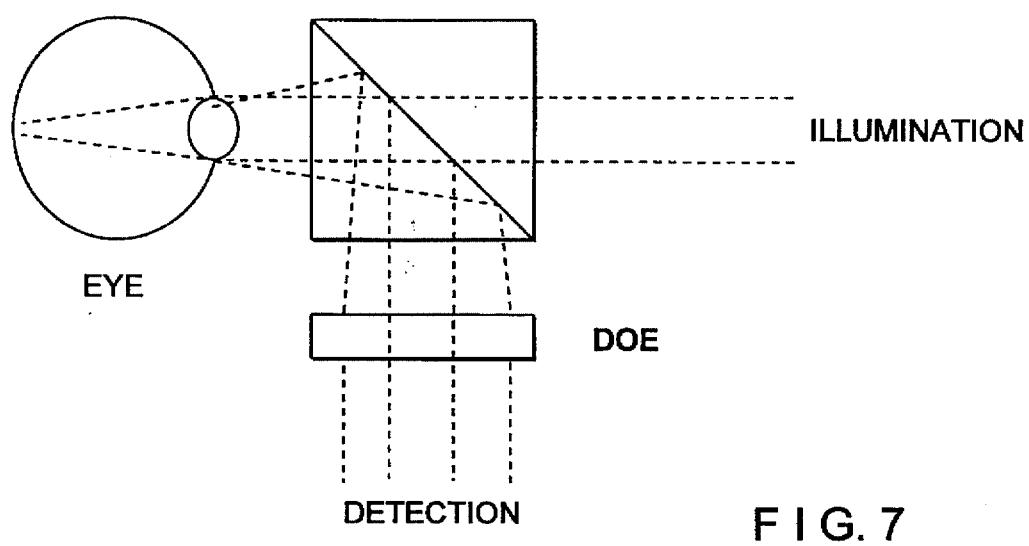
FIG. 7 is a schematic view of the arrangement of a DOE for unifying the measurement light components proceeding from different boundary surfaces.

In FIG. 7, the wavefronts of the measurement light components preceding from different boundary surfaces of the eye are adapted to one another by the DOE arranged in a detection beam path, while the illumination light falls via a beam divider.

Figure 8:
FIG. 8 shows an exemplary profile of a phase fresnel lens.

FIG. 8 shows a conventional phase fresnel lens. In a phase fresnel lens the height of the serrations corresponds approximately to the order of magnitude of the measurement light wavelengths resulting in bending effects.

The ratio between affected and unaffected beam components, i.e., the efficiency of the DOE, can be optimized in a particularly advantageous manner via the selected profile depth of the phase fresnel lens, but also by means of a corresponding fabrication of the phase fresnel lens with omitted structured zones or sectors.

It is conceivable to use a plurality of different DOE's, for example, to compensate for relative signal strengths of the cornea signal and retina signal which fluctuate from patient to patient.

The controlling and evaluating unit 19 shown in FIG. 1 also contains supply and (filter) amplifier units for the detector 17.

Additional communications connections of the unit 19 for other devices, in particular for additional controlling and evaluating units and additional measuring devices, e.g., ophthalmometers or keratometers, can also be provided.

While the foregoing description and drawings represent the preferred embodiments of the present invention, it will be obvious to those skilled in the art that various changes and modifications may be made therein without departing from the true spirit and scope of the present invention.

What is claimed is:

1. An arrangement for measuring intraocular distances between different optical boundary surfaces of the human eye by at least one interferometric measurement system, said arrangement further comprising:

at least one diffractive optical element (DOE) for at least one of the following purposes: a) dividing an illumination beam path into partial beam paths for different boundary surfaces; b) allowing the combination and mutual adaptation of the wavefronts of measurement light components proceeding from different boundary surfaces; and c) adaptation of the wavefronts of measurement light components proceeding from different boundary surfaces of the eye to the wavefront of the measurement light of at least one interferometric reference arm.

2. The arrangement according to claim 1, wherein the DOE is constructed in the manner of a phase fresnel lens.

3. The arrangement according to claim 1, including a coherent illumination device for illuminating the eye via said interferometric measurement system having means for the measurable adjustment of the difference in optical wavelength between two interferometric partial beam paths and means for at least one of observing and detecting the interfering radiant components reflected by different boundary surfaces of the eye, said diffractive optical element being provided for at least one of the following purposes: a) dividing an illumination beam path into partial beam paths for different boundary surfaces; and b) allowing the combination and mutual adaptation of the wavefronts of measurement light components proceeding from different boundary surfaces of the eye.

4. The arrangement according to claim 1, including a coherent light source with changeable wavelength, at least one reference arrangement with a fixed optical wavelength difference for generating a defined, wavelength dependent phase difference, and at least one measurement arrangement for generating a wavelength-dependent phase difference between radiant components reflected by different boundary surfaces, one of said different boundary surfaces being a first boundary surface of the eye and another of said different boundary surfaces being taken from the group consisting of a second boundary surface of the eye and an external reference surface, wherein the signals of the measurement and reference arrangement are combined to generate beat signals, said DOE being provided for at least one of the following purposes: a) dividing at least one illumination beam path into partial beam paths for different boundary surfaces; b) allowing combination and mutual adaptation of the wavefronts of measurement light components proceeding from different boundary surfaces of the eye; and c) adaptation of the wavefronts of measurement light components proceeding from different boundary surfaces of the eye to the wavefront of the measurement light of at least one interferometric reference arm.

5. The arrangement according to claim 1, wherein the reflected light is brought to interference with light reflected by a preferably adjustable reference surface of a reference channel for different boundary surfaces of the eye, and at least one DOE is provided for at least one of the following purposes: a) dividing at least one illumination beam path into partial beam paths for different boundary surfaces; and b) allowing the combination and mutual adaptation of measurement light components proceeding from different boundary surfaces of the eye to the phase front of the reflected light proceeding from the reference surface of the reference channel.

6. The arrangement according to claim 1, wherein the DOE is arranged between the eye and illumination and measurement beam paths.

7. The arrangement according to claim 6, wherein the DOE is arranged between at least one beam divider and the eye.

8. The arrangement according to claim 7, wherein the beam divider divides into an illumination beam path and a measurement beam path.

9. The arrangement according to claim 1, wherein the DOE is located in a measurement beam path which is cut out from an illumination beam path for the eye.

10. The arrangement according to claim 1, wherein the DOE is arranged in an illumination beam path for the eye upstream of a beam divider which cuts out measurement light from the illumination beam path.

11. The arrangement according to claim 1, wherein the DOE performs at least one of the following: a) it divides the illumination light into an unaffected component and at least one convergent component; and b) it collimates the measurement light components for adapting the wavefronts.

12. The arrangement according to claim 1, wherein a convergent component of the illumination beam path is focussed on the corneal vertex.

13. The arrangement according to claim 1, wherein a convergent component of the illumination beam path is focussed on the focal point of the convex corneal image.

14. The arrangement according to claim 1, wherein said arrangement provides focussing of a convergent component of the illumination light on the center of curvature of the convex corneal image.

15. The arrangement according to claim 1, wherein said arrangement provides focussing on at least one additional boundary surface of the eye.

16. The arrangement according to claim 1, wherein said arrangement provides a combination of the diffractive optical element with at least one additional imaging element.

17. The arrangement according to claim 16, including a combination of a plurality of DOE's.

18. The arrangement according to claim 16, wherein the imaging element is at least one lens.

19. The arrangement according to claim 1, wherein at least one of an intensity ratio between an unaffected component and an affected component of the illumination beam path and an intensity ratio of the measurement light components of different boundary surfaces of the eye is determined by the construction of the diffractive optical element.

20. The arrangement according to claim 1, wherein at least one of an intensity ratio between an unaffected component and an affected component of the illumination beam path and an intensity ratio of the measurement light components of different boundary surfaces of the eye is varied by an optional use of differently constructed diffractive optical elements.

21. The arrangement according to claim 1, wherein overlapped partial beam paths reflected by different regions of the eye are imaged in at least one of a detection plane and observation plane via a lens arrangement after repeatedly passing through the optical element.

* * * * *